United States Patent [19]

Beny et al.

[11] Patent Number: 4,546,644

[45] Date of Patent: Oct. 15, 1985

[54] METHOD AND APPARATUS FOR LOCATING THE DYNAMIC AXIS OF A SPHERE

[76] Inventors: Janos Beny, 3202 Singingwood Dr., Torrance, Calif. 90505; David E. Tompkins, 705 Pruitt Dr., Redondo Beach, Calif. 90278

[21] Appl. No.: 569,121

[22] Filed: Jan. 9, 1984

[51] Int. Cl.⁴ ............................................. G01M 1/26
[52] U.S. Cl. ........................................ 73/65; 73/461; 273/213
[58] Field of Search ............ 73/65, 66, 460, 461, 73/472; 273/32 B, 32 H, 213

[56] References Cited

U.S. PATENT DOCUMENTS

| | | | |
|---|---|---|---|
| 2,946,224 | 7/1960 | Yamaguchi | 73/461 |
| 4,111,038 | 9/1978 | Olson et al. | 73/65 |
| 4,233,846 | 11/1980 | Taylor | 73/460 |

FOREIGN PATENT DOCUMENTS 0381936  8/1973  U.S.S.R. ................. 73/65

*Primary Examiner*—Charles A. Ruehl
*Attorney, Agent, or Firm*—Nilsson, Robbins, Dalgarn, Berliner, Carson & Wurst

[57] ABSTRACT

The dynamic axis of a sphere, e.g. golf ball, is located by spinning the sphere at high speed while it is supported on a low friction-bearing surface, thus allowing the desired stable axis to align itself with the spin axis. Markings indicative of the location of the stable axis are applied to the sphere. The spinning operation also indicates the degree of existing eccentricities in the sphere.

7 Claims, 7 Drawing Figures

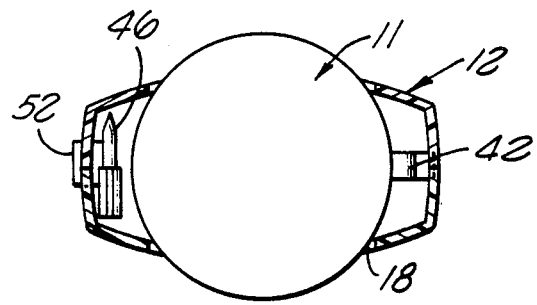
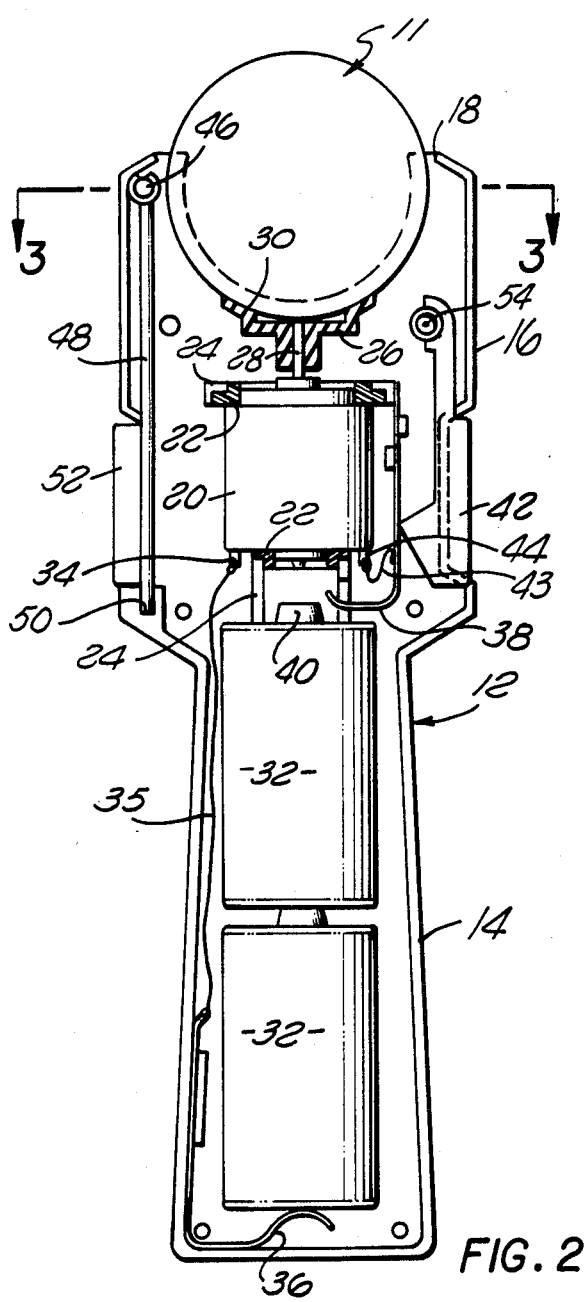
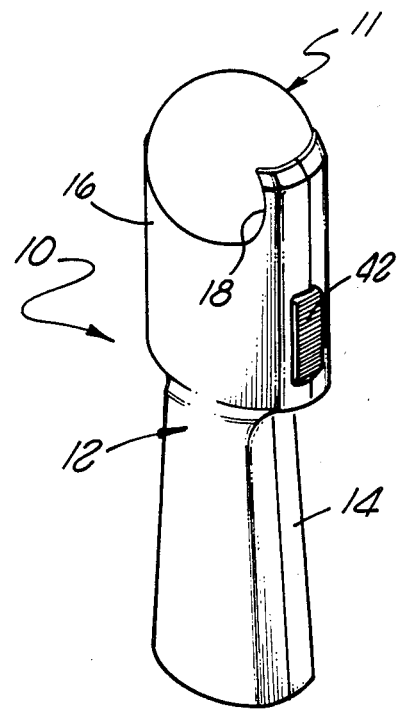
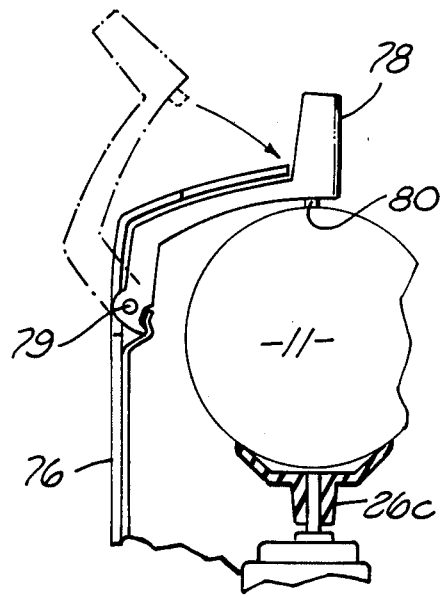

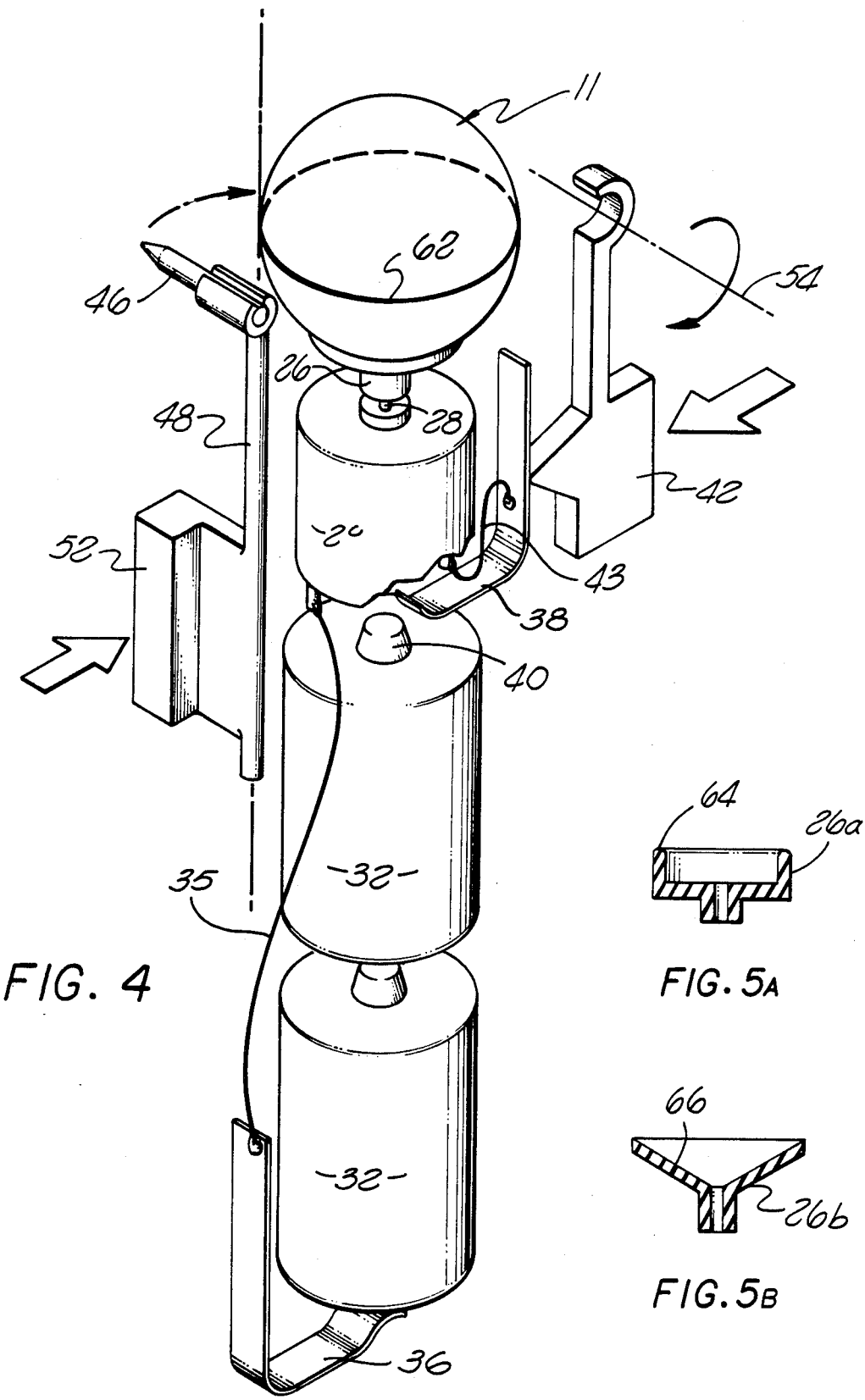

METHOD AND APPARATUS FOR LOCATING THE DYNAMIC AXIS OF A SPHERE

BACKGROUND OF THE INVENTION

1. Field of the Invention

The present invention pertains to methods and apparatus for testing ball eccentricity and locating the dynamic axis of a sphere and is more particularly directed to method and apparatus for testing and marking a ball such that a player is able to propel the ball with its eccentricity located to accommodate motion along the intended path of travel.

2. State of the Prior Art

Traditionally golf balls have been manufactured by winding a ribbon of resilient material in multiple layers about a hard central core and then encapsulating the windings in a hard outer shell. More recent methods of golf ball manufacture have sought to eliminate the winding process in favor of molding processes whereby a solid spherical layer of a resilient material is molded about a central core. The resilient layer is then encapsulated in the conventional outer shell.

In accordance with the present invention, it has been discovered that in various manufactures, golf balls sometimes exhibit unpredictable dynamic characteristics even when stroked in a consistent manner. For example, an unpredictable ball can be detected by stroking it on a level putting green with a mechanical plunger device capable of delivering a repeatedly uniform stroke. To varying degrees, the golf ball may deviate unpredictably from the expected straight travel path.

At the present time, it is theorized that the unpredictable behavior of a golf ball is often due to an imperfection of balance, namely an eccentricity in the ball. Such inaccuracy of balance occurs in a golf ball having a center of gravity offset from the geometric center of the ball. Consequently, when such a ball is rolled over a surface, forces develop causing the ball to deviate from a straight line of travel. To attain the truest path of travel, an eccentric ball is to be struck such that the dynamic axis tumbles as the ball turns. When a golf ball is randomly stroked during normal play, the undesirable deviations considered above may well hinder competitive play. Consequently, in accordance with the present invention, a need exists for a system to effectively test balls and mark them for more consistent movement.

SUMMARY OF THE INVENTION

According to the present invention, a sphere such as a golf ball is supported for substantially free rotation about any axis containing its geometric center and is spun about that axis. For example, the ball may be supported on a cup having a low friction-bearing surface and hand-held for resilient support. A spin is imparted to the ball by rotating the cup about an axis containing the sphere's geometric center. Movement of the ball on the cup indicates an eccentricity. The lower the speed to prompt movement, the greater the eccentricity. Consequently, the ball moves to find an equilibrium position relative to the spin axis in response to forces induced by the spin.

The spin axis of the ball at the equilibrium position may be referred to as the dynamic axis of the ball, i.e. the axis at which minimal precession forces arise because both the center of gravity and geometric center of the sphere lie in a perpendicular plane. Accordingly, by marking the ball, it is possible to position it for play to achieve more predictable dynamic behavior.

A compact portable device for detecting eccentricity and for marking a ball accordingly has a cup support coupled to a small battery-powered motor mounted in a hand-held housing. The marking device is provided to be moved to contact a ball placed on the cup. By operation of the device, the stable roll axis of a golf ball may be quickly and easily determined.

The ball is seated on the cup, hand-held in an upright position. Power is switched to the motor. As the ball turns, it will be observed to move if there is eccentricity. If movement occurs at low speed, it may be best to reject the ball for use in play. When the ball moves to a stable spinning position on the spinning cup, the dynamic axis is indicated. The marker device is then moved to contact the ball designating the dynamic axis and providing a guide for the correct alignment of the ball in relation to its intended direction of travel or roll.

BRIEF DESCRIPTION OF THE DRAWINGS

FIG. 1 is a perspective view of a hand-held device for testing a golf ball and locating the dynamic axis according to this invention;

FIG. 2 is a sectional view in elevation of the device of FIG. 1;

FIG. 3 is a section taken along line 3—3 in FIG. 2;

FIG. 4 is an exploded view of the device of FIG. 3;

FIG. 5A is a first alternate cup form for use in the device of FIG. 3;

FIG. 5B is a second alternate cup form for use in the device of FIG. 3; and

FIG. 6 is a fragmentary view similar to FIG. 2 illustrating an alternative marking structure.

DETAILED DESCRIPTION OF THE PREFERRED EMBODIMENT

With reference to the drawings and FIG. 1 in particular, a golf ball marking device 10 constructed according to the present invention is illustrated. A housing 12 defines the structure and receives a golf ball 11. The housing 12 comprises mated halves and defines a lower, elongated handle-shaped portion 14 and an upper portion 16 including an opening 18 at the upper end dimensioned for receiving the golf ball 11. In operation, the ball 11 is revolved by a D.C. motor 20 (FIG. 2) mounted in the housing 12 on grommets 22 which fit into collar mounts 24. Thus, eccentricity is detected by spinning the ball and it also is aligned for marking.

A cup 26 (FIG. 2) holds the ball 11 and is fixed on the output shaft 28 of the motor 20. The cup 26 defines a spherical bearing surface 30, radially symmetrical to the output shaft 28 to receive a golf ball 11 set within the opening 18. The bearing surface 30 is dimensioned for adequate and stable support of the ball 11 while the housing 12 is held upright by manually gripping the lower portion 14. The area of contact between the bearing surface 30 and the golf ball is minimized to reduce frictional engagement of the cup with the ball. Note that if the structure is not hand-held, a resilient mounting will likely be desirable.

The D.C. motor 20 may comprise a three-volt unit of a type commonly used for toys. It is powered by a pair of 1.5 volt stacked batteries 32 connected in series. To make the circuit, the negative terminal 34 of the motor 20 is connected by a conductor 35 to a spring contact 36 engaging the negative terminal of the lower battery 32.

A normally open switch 38 (middle right, FIG. 2) is movable into electrical contact with the positive terminal 40 of the upper battery 32 by means of a pivotable lever 42. The circuit is completed by a second conductor 43 connecting the switch contact 38 to the positive terminal 44 of the motor 20.

A marker element 46 which may comprise a pencil lead or any other marker which is mounted at the upper end of a pivot 48 (FIG. 4) rotatable within a socket 50 (FIG. 2) in response to manual pressure applied to a tab 52 extending from the pivot through an opening in the housing 12. The marker element 46 is normally spaced from the surface of a golf ball 11 on the cup 26 and can be brought into tangential marking contact with the ball surface by manual rotation of the marker pivot 48.

The dynamic axis of a golf ball is determined and marked by simple use of the marker device 10. A golf ball 11 is seated on the bearing surface 30 of the cup 26 as in FIG. 2 while the device is held in upright position. The switch lever 42 is manually depressed to pivot about its axis 54 as suggested by the arrows in FIG. 4, thus urging the normally open switch contact 38 into electrical contact with the dry cell terminal 40. Accordingly, the motor 20 is energized rotating the cup 26 and accelerating to a relatively high speed, typically several thousand R.P.M. The rotation of the cup is imparted to the golf ball 11 by virtue of frictional contact with the bearing surface 30 so that the ball 11 spins with the cup 26 about a spin axis concentric with the shaft 28 of the motor 32.

If the center of gravity of the rotating golf ball is eccentric relative to the ball's geometric center, internal forces are induced by the rotation causing the golf ball to move to an equilibrium position relative to the spin axis. As a result, the ball will be observed to move about its geometric center relative to the bearing surface 30. This movement or shifting of the ball indicating eccentricity is distinct from the ball's spin. The movement may occur about any axis containing the geometric center of the ball until the equilibrium position is found, as visually determined by a lack of further shifting of the ball relative to the cup 26. Thereafter, the ball merely rotates about the spin axis along with the cup 26.

The alignment of the ball 11 as described above may be described mathematically; however, the phenomenon is much like the operation of a toy top. The rotational forces simply shift the ball 11, gradually aligning the eccentricity until it approaches zero. At that position, the center of mass may be above or below the equator; however, the ball is dynamically balanced.

With the ball stabilized, the marker point 46 may be brought into contact with the surface of the golf ball 11 by pressing on tab 52 as indicated by the arrow in FIG. 4 while the ball is turning. As a result, a circle 62 is scribed on the ball. Ideally, the marker 46 is mounted so that the circle 62 is at the equatorial plane containing the geometric center of the ball 11. The most stable roll axis of the golf ball 11 is through the geometric center of the ball and in the plane defined by the circle 62. The stable roll axis is perpendicular to the dynamic spin axis attained on the cup 26. Accordingly, a golf player is able to position the golf ball in play with the plane of the circle 62 aligned with the ground surface and perpendicular to the intended path. When the ball is so stroked, it will roll in its most true pattern.

Considering the use of a ball, suppose it is stroked as in a putt. If the ball has eccentricity, it is to be positioned with the rotational axis of the ball as described above. Otherwise, imbalance of the hemispheres will unpredictably offset the roll of the ball from a true path detracting from the accuracy of the putt.

The alignment also is significant as in driving a golf ball. Normally, the ball is stroked to produce substantial top spin. If an eccentricity is not aligned for dynamic balance, the ball will follow a deviated path.

Of course, there are various structural alternatives to the apparatus as described above for testing balls and marking them for best performance. For example, the cup 26 shown in FIGS. 2 and 4 may take various alternate forms such as the cylindrical cup 26a of FIG. 5A or the conical cup 26b of FIG. 5B. In FIG. 5A, the ball makes line contact with a rim 64 while in FIG. 5B the ball makes line contact with the conical surface 66. Both of these alternate cup forms support the ball while fixing the geometric center of the ball in alignment with the spin axis of the cup as established by the output shaft of the motor. Still other cup forms will become apparent which meet these requirements.

Other marking patterns and structures are also of interest. For example, the alternative structure of FIG. 6 shows a ball 11 on a cup 26c in a housing 76 generally similar to that described above. In the structure of FIG. 6, a marking arm 78 is pivotally mounted at point 79 to swing in a vertical plane carrying a marker 80 to contact an axial spot at the dynamic axis. Thus, the dynamic axis of rotation is marked by a single dot. In use, a ball so marked is to be stroked with the dot at the top of the ball so that it will tumble about the dynamic axis.

It will be evident to those possessing ordinary skill in the art that devices other than the particular device 10 shown in the drawings may be constructed for carrying out the method of this invention. For example, for the mass processing of golf balls according to the invented method, the golf ball may be floated on a cushion of air and rotated at high speed by means of tangential air jets. Suitable markings or indicia may be applied to the ball surface after equilibrium is reached by means such as ink jet devices or lasers. It will be further understood that the stable roll axis of the golf ball determined by the method of this invention may be indicated by marking the ball in a variety of ways and is not limited to a circle 62 or dot as illustrated in the drawings.

It will be understood that many changes and modifications may be made to the method and apparatus of the invention by those having ordinary skill in the art and that the description and drawings of the preferred embodiment are by way of illustration and not limitation of the scope of the following claims.

What is claimed is:

1. An apparatus for locating the orientation of a golf ball for substantially true-roll stroking, comprising:
    a cup support means defining a bearing surface to engagingly receive said golf ball for substantially free movement thereon;
    housing means for supporting said cup for rotation and defining an opening for receiving said cup support means in radially symmetrical relationship whereby at least an upper portion of said golf ball is accessible for marking; and
    motor means fixed in said housing means for rotating said cup support means with said golf ball thereon to spin said golf ball into stable alignment for marking.

2. An apparatus according to claim 1 further including switch means affixed to said housing means for controlling said motor means.

3. An apparatus according to claim 2 wherein said housing means further defines a compartment for receiving batteries for powering said motor means.

4. The apparatus according to claim 1 further including marker means comprising a pivotally mounted member and a marker supported thereby to contact said sphere.

5. A method for testing and marking a golf ball, comprising the steps of:
   supporting the golf ball for substantially free rotation about any axis containing its geometric center;
   imparting a spin to said golf ball about a spin axis containing the geometric center of the golf ball to thereby cause eccentricity of the golf ball to move it toward an equilibrium position in response to forces induced by said spin; and
   marking the golf ball to identify a plane perpendicular to the spin axis in the equilibrium position for reference in stroking the golf ball.

6. The method according to claim 5 wherein said marking step involves the placement of a dot on said golf ball.

7. The method of claim 5 wherein said marking step comprises the step of applying marker means to the surface of the golf ball while it is spinning to inscribe a circle on the golf ball.

* * * * *